United States Patent [19]

Jurcik et al.

[11] Patent Number: 5,714,678

[45] Date of Patent: Feb. 3, 1998

[54] METHOD FOR RAPIDLY DETERMINING AN IMPURITY LEVEL IN A GAS SOURCE OR A GAS DISTRIBUTION SYSTEM

[75] Inventors: Benjamin Jurcik, Lisle; James McAndrew, Lockport; Dmitry Znamensky, Darien, all of Ill.

[73] Assignee: American Air Liquide Inc., Walnut Creek, Calif.

[21] Appl. No.: 757,752

[22] Filed: Nov. 26, 1996

[51] Int. Cl.$^6$ .................................................. G01N 7/00
[52] U.S. Cl. ................................... 73/31.03; 73/23.2
[58] Field of Search .......................... 73/31.03, 23.2, 73/863.83, 864.81

[56] References Cited

U.S. PATENT DOCUMENTS

| | | |
|---|---|---|
| 4,430,886 | 2/1984 | Rood . |
| 4,523,452 | 6/1985 | Brayman . |
| 4,587,619 | 5/1986 | Converse, III et al. . |
| 4,640,122 | 2/1987 | Héraud et al. . |
| 4,692,621 | 9/1987 | Passaro et al. ............................ 250/343 |
| 4,715,214 | 12/1987 | Tveter et al. . |
| 4,879,912 | 11/1989 | Suckow . |
| 4,915,613 | 4/1990 | Landis et al. . |
| 4,942,758 | 7/1990 | Cofield . |
| 4,971,100 | 11/1990 | Ohmi ......................................... 137/334 |
| 5,092,937 | 3/1992 | Ogura et al. . |
| 5,113,705 | 5/1992 | Earnhardt . |
| 5,117,675 | 6/1992 | Notoyama et al. . |
| 5,178,651 | 1/1993 | Balma et al. ................................. 55/20 |
| 5,325,705 | 7/1994 | Tom ........................................... 73/31.03 |
| 5,330,652 | 7/1994 | Goldman et al. . |
| 5,412,978 | 5/1995 | Boon et al. . |
| 5,447,053 | 9/1995 | Ohmi ........................................... 73/31.03 |
| 5,475,619 | 12/1995 | Sugano et al. . |
| 5,493,902 | 2/1996 | Glidewell et al. . |
| 5,497,652 | 3/1996 | Ohmi ........................................... 73/31.03 |
| 5,590,711 | 1/1997 | Ishida et al. ................................. 165/179 |
| 5,604,298 | 2/1997 | Dosoretz et al. ............................ 73/23.2 |

FOREIGN PATENT DOCUMENTS 5-140777  6/1993  Japan .

OTHER PUBLICATIONS

Jurcik et al, "The Effect of Baking on the Dry Down of UHP Distribution Systems: From Laboratory to Industrial Scale via Numerical Simulation", Proceedings—Institute of Environmental Sciences, 1995 meeting.

McAndrew et al, "Using Simulation to Optimize Gas Distribution System Cost and Performance", Journal of the IES, Sep./Oct. 1994, pp. 30–39.

(List continued on next page.)

*Primary Examiner*—Hezron E. Williams
*Assistant Examiner*—Jay L. Politzer
*Attorney, Agent, or Firm*—Burns, Doane, Swecker and Mathis, L.L.P.

[57] ABSTRACT

Provided is a novel method for rapidly determining an impurity level in a gas source. A gas source and a measurement tool are provided for measuring an impurity level in a gas flowing from the gas source. The measurement tool is in communication with the gas source through a sampling line. The sampling line has a gas inlet disposed upstream from a gas outlet. The sampling line is baked according to a baking strategy, such that when baking is terminated, a concentration profile of the impurity in the sampling line contains a first region and a second region. In the first region, extending from the gas inlet to a point downstream from the inlet, the vapor phase concentration of the impurity is less than the vapor phase concentration of the impurity in the gas entering the sampling line. In the second region, located downstream from the first region and extending to the gas outlet, the vapor phase concentration of the impurity is greater than the vapor phase concentration of the impurity in the gas entering the sampling line. A method for rapidly determining an impurity level in a gas distribution system which delivers gas to a point of use is also provided. Particular applicability is found in the semiconductor processing industry to measure impurities in gases delivered to processing tools.

14 Claims, 6 Drawing Sheets

OTHER PUBLICATIONS

Liehr et al, "Concepts in Competitive Miroelectronics Manufacturing," J. Vac. Sci. Technol. B 12(4), Jul./Aug. 1994, pp. 2727–2740.

K. Tatenuma et al, Buneski 223, 393 (1994).

Miyazaki et al, "Determination of Trace Impurities in Corrosive Gases by Gas–Phase FTIR," Bull. Chem. Soc. Jpn. 66,3508–3510(1993), Nov. 1993, vol. 68, No. 11, pp. 3508–3510.

Tatenuma et al, "Quick Acquisition of Clean Ultrahigh Vacuum by Chemical Process Technology," J. Vac. Sci. Technol. A 11(4), Jul./Aug. 1993, pp. 1719–1724.

Miyazaki et al, "Analysis of Trace Moisture in HCl by Gas–Phase FTIR," Bull. Chem. Soc. Jpn. 66,969–971(1993), Mar. 1993, vol. 66, No. 3, pp. 969–971.

Venet, paper presented at 1991 Fall AICHE Conference, pp. 26–28.

METHOD FOR RAPIDLY DETERMINING AN IMPURITY LEVEL IN A GAS SOURCE OR A GAS DISTRIBUTION SYSTEM

BACKGROUND OF THE INVENTION

1. Field of the Invention

The present invention relates to a novel method for rapidly determining an impurity level in a gas source. The present invention also relates to a method for rapidly determining an impurity level in a gas distribution system.

2. Description of the Related Art

The manufacture of integrated circuits (IC's) involves processes in which semiconductor wafers are contacted with various gases. Such processes include, for example, chemical vapor deposition (CVD), diffusion, oxidation, sputtering, rapid thermal processing, etching and ion implantation processes. The gases can be stored in, for example, gas cylinders, bulk storage systems or supplied by an onsight separation plant.

Because of the high sensitivity of IC devices to impurities, the impurity level in the manufacturing environment plays a crucial role in the yield, and hence, in the profitability of a wafer fabrication facility (wafer fab). Microelectronics manufacturers require extremely high purity gases, for example ultra-high purity (UHP) gases, delivered to the point of use (i.e., to the processing tool). Gas source suppliers and gas distribution system installers are therefore required to certify performance of a gas source or a gas distribution system in terms of impurity levels in the gas source or gas distribution system.

For microelectronics applications, impurity measurements in the parts per billion (ppb) to sub ppb range are generally required. Thus, the use of sophisticated analytical instrumentation, such as atmospheric pressure ionization mass spectrometers (APIMS), is required. Moreover, in making the requested measurements, great care in the sampling procedure is necessary. As a result, the costs associated with the analytical equipment and the manpower necessary to perform the certification measurements represent a significant investment. Given the industrial trend towards decreasing the construction time of wafer fabs, reductions in time and resources necessary for certification of a gas source or gas distribution system have substantial value.

Moisture level measurement in industrial scale systems is typically carried out with the use of a sampling line connected between the gas source or gas distribution system and a measurement tool. The sampling line takes a gas sample from the gas source or from a given point in the gas distribution system and delivers it to the measurement tool, where the impurity level is measured.

The sampling line itself contributes to the measured impurity level, and hence, the gas must be purged through the sampling line until the impurity value measured by the measurement tool represents the actual value of the gas source or the gas distribution system. This is especially true for impurities which have extremely slow response times (e.g., moisture) due to the strong interaction of the impurity with the inner surfaces of the gas distribution system and sampling line.

The interaction of the impurity to be measured with the surfaces of the gas distribution system can affect both the length of time it takes to dry down a gas distribution system as well as the sensitivity of the measurement tool that samples the gas through the sampling line. This effect has been recognized in a publication by McAndrew et al (*Using Simulation to Optimize Gas Distribution System Cost and Performance*, Journal of the IES, September/October 1994, pp. 30–39), which describes how the time delay for a moisture upset to travel through a sampling line affects the size and duration of upset that can be detected.

Various procedures have been used in the past to decrease the time required to measure the value of an impurity in a gas distribution system via a sampling line. These procedures include, for example, use of a sampling line constructed from a material that interacts less strongly with the impurity of interest than the distribution system itself (see, Venet et al, from fall 1991 AICHE conference (1992), pp. 26–28), and baking of the system at an elevated temperature to drive off adsorbed impurities from the surfaces making up the sampling line (see, Jurcik et al, *The Effect of Baking on the Dry Down of UHP Distribution Systems: From Laboratory to Industrial Scale via Numerical Simulation*, from proceedings of the 1995 IES meeting (1995)).

However, the above procedures are ineffective to minimize the time required to bring the concentration of the impurity measured at the outlet of the sampling line to the same level as in the gas introduced through the sampling line inlet. For example, while construction of the sampling line out of a material that interacts less strongly with the impurity of interest may decrease the time required to measure the actual value of that impurity, currently available tubing materials and surface finishes exhibit strong interactions with moisture. Thus, measurement time is substantial.

Furthermore, although baking of the sampling line can be effective in decreasing measurement time, artificially low values may be observed for extended periods of time if care is not taken in the selection of an appropriate baking strategy. In such a case, the true impurity level in the gas source or gas distribution system is not measured, and the gas source or gas distribution system is certified at a lower than actual value.

To meet the requirements of the semiconductor processing industry, and to overcome the disadvantages of the related art, it is an object of the present invention to provide a novel method for determining impurity levels in a gas source or a gas distribution system. The inventive method allows for accurate and rapid measurements of impurity concentration. Thus, certification of a gas source or a gas distribution system can be performed with a greater degree of accuracy and more quickly than was previously possible. Substantial cost savings in the set-up of wafer fabs can be realized.

SUMMARY OF THE INVENTION

The foregoing objectives are met by the methods of the present invention. According to a first aspect of the invention, a novel method for rapidly determining an impurity level in a gas source is provided. The method includes providing a gas source and a measurement tool for measuring an impurity level in a gas flowing from the gas source. The measurement tool is in communication with the gas source through a sampling line. The sampling line has a gas inlet disposed upstream from a gas outlet. The sampling line is baked according to a baking strategy, such that when baking is terminated, a concentration profile of the impurity in the sampling line contains a first region and a second region. In the first region, extending from the gas inlet to a point downstream from the inlet, the vapor phase concentration of the impurity is less than the vapor phase concentration of the impurity in the gas entering the sampling line. In the second region, located downstream from the first region and extending to the gas outlet, the vapor phase concentration of the impurity is greater than the vapor phase concentration of the impurity in the gas entering the sampling line.

According to a second aspect of the invention, a method for rapidly determining an impurity level in a gas distribution system is provided. This second aspect is similar to the above-described method, except a gas distribution system for delivering a gas to a point of use is connected to the gas source. The measurement tool is in communication with the gas distribution system through the sampling line, such that gas flows from the gas source through the gas distribution system and the sampling line to the measurement tool.

BRIEF DESCRIPTION OF THE DRAWINGS

The objects and advantages of the invention will become apparent from the following detailed description of the preferred embodiments thereof in connection with the accompanying drawings, in which.

DETAILED DESCRIPTION OF THE PREFERRED EMBODIMENTS OF THE INVENTION

The invention provides an effective method for rapidly and accurately determining an impurity level in a gas source or a gas distribution system. Applicants have surprisingly and unexpectedly determined that baking of a sampling line can be very effective in decreasing the time required to measure the actual concentration of the gas source or gas distribution system if the duration and intensity of the baking are carefully controlled.

The invention has two substantial benefits over known methods for detecting an impurity in a gas source or gas distribution system. First, more rapid determination of the impurity level in a gas source or a gas distribution system is possible, and second, improper certification at artificially low levels can be prevented.

As used herein, the term "gas source" refers to any gas stored in a cylinder or in a bulk storage system, either in a gaseous or liquified state. That term also refers to gas produced in a gas manufacturing plant.

Also as used herein, "gas distribution system" refers to the gas piping connecting the gas source with a point of use, such as a semiconductor processing tool. The gas distribution system also encompasses the components between the gas system and the point of use, such as regulators, valves, flowmeters, etc.

Also as used herein, the term "baking strategy" refers to the controlled temperature versus time profile of the sampling line.

Also, the terms "moisture" and "water vapor" herein have been used interchangeably.

The gas source is preferably an ultra high purity (UHP) gas source which can be used in the manufacture of semiconductor devices. Thus, the gas distribution system must be compatible with the purity of gas introduced therein. Preferable gases used in connection with the inventive method include nitrogen ($N_2$), oxygen ($O_2$), argon (Ar) and helium (He). This list, however, is in no way limitative.

The impurity to be measured can be, for example, water vapor, a hydrocarbon (e.g., $CH_4$), a metal, NO, CO or $CO_2$. The impurity to be measured is preferably water vapor.

In order to measure impurities in a gas obtained from the gas source or gas distribution system, the gas source or gas distribution system is placed in communication with a measurement tool. Any fast response, trace level measuring instrument sensitive to the impurity of interest can be used. Suitable measurement tools are known in the art, and include, for example, atmospheric pressure ionization mass spectrometers (APIMS) and tunable diode laser absorption spectrometers (TDLAS).

A gas sample from the gas source or gas distribution system is delivered to the measurement tool through a gas sampling line. The gas sampling line is preferably constructed from 316L electropolished stainless steel (EP SS), in a diameter which is selected dependent upon the specific measurement tool being used. Flowrate and pressure of the gas sample introduced into the sampling line should be selected based upon the specifications and requirements of the measurement tool. For example, in the case of an APIMS measuring moisture, the gas sample pressure is preferably in the range of from about 1 to 12 Bar, and the sample flowrate is preferably in the range of from about 1 to 20 slm.

In order to thermally regulate the sampling line, one or more heaters for baking the sampling line and a controller for controlling the temperature of the sampling line according to a desired baking strategy are provided. The heater should have the capability of baking the sampling line up to a temperature of about 100° C. with an accuracy of about ±2° C. Any type of heater which can control the temperature of the sampling line according to the desired baking strategy can be used. Examples of suitable heaters include, for example, resistance-type heaters and heat lamps. A resistance-type heater which surrounds the sampling line (e.g., heating tape) is preferred.

In measuring an impurity level in a gas source, a gas sample is taken from the gas source through the sampling line. When the gas source is in a gas cylinder or a bulk storage device, the gas sample is typically withdrawn directly through the gas cylinder valve or bulk storage device valve, or immediately downstream therefrom, for example through a "T-type" fitting. In the case of a gas manufacturing plant, the gas sampled can be withdrawn from a final product storage tank or a final product outlet line.

In the case of a gas distribution system, sampling can be performed at various points along the distribution system between the gas source and the point of use.

Figure 1:
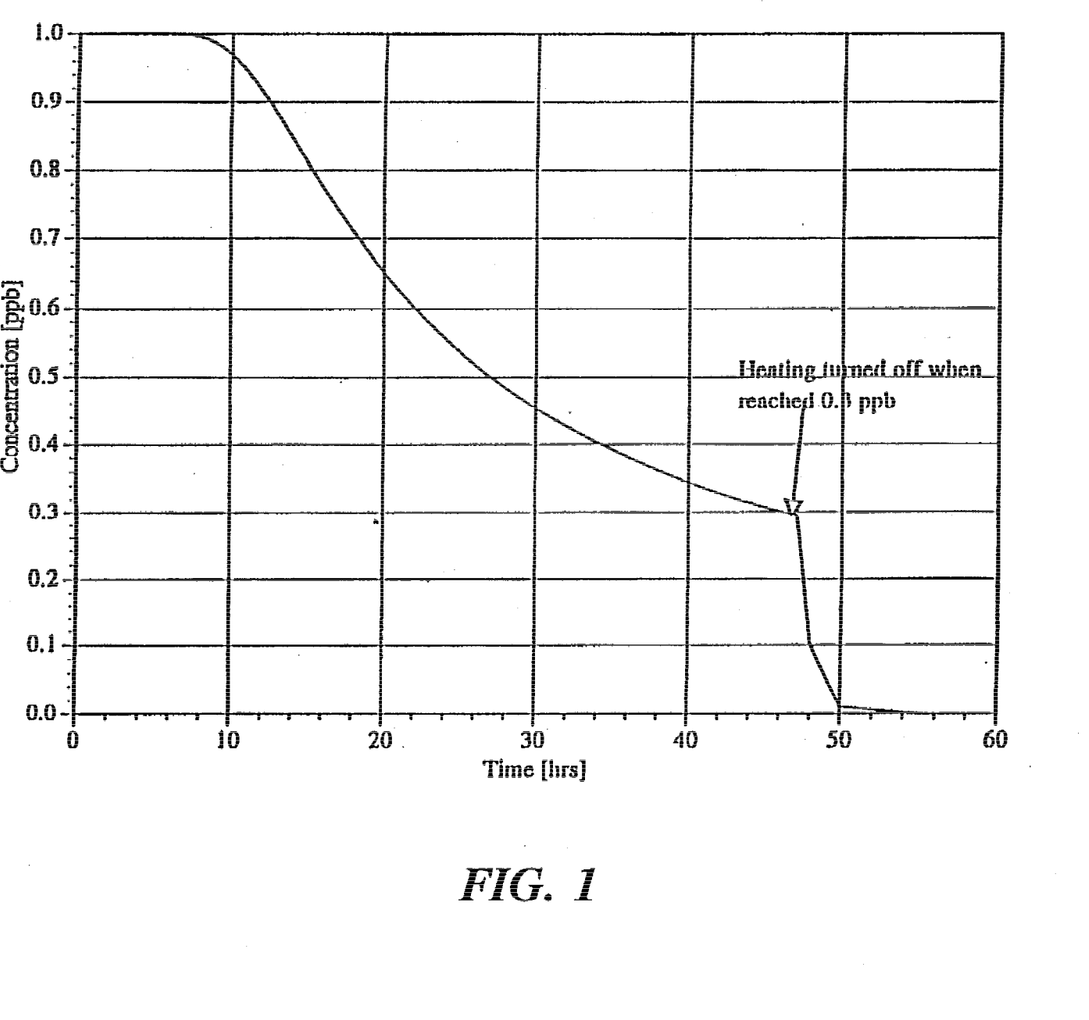
FIG. 1 is a graph of moisture concentration versus time for a sampling line, showing the effect of sampling line baking on measured moisture concentration.

FIG. 1 illustrates the results of a simulation example in which an artificially low certification would be expected.

The simulated drydown of a 50 foot, ¼ inch (O.D.) 316L electropolished stainless steel (EP SS) sampling line which is baked at 100° C. is shown. The source gas in this simulation contains 0.25 parts per billion (ppb) water vapor. For the conditions for which the simulation was performed, the baking is turned off after about 45 hours. At that time, the measured water vapor concentration is substantially reduced. The impurity level remains well below 0.1 ppb for an extended period of time, for example, greater than one week. Behavior of this nature has been observed both in simulation and in actual measurements. As a result of these drydown characteristics, certification of a gas source and/or a gas distribution system at a level lower than the actual level would be expected.

Figure 2:
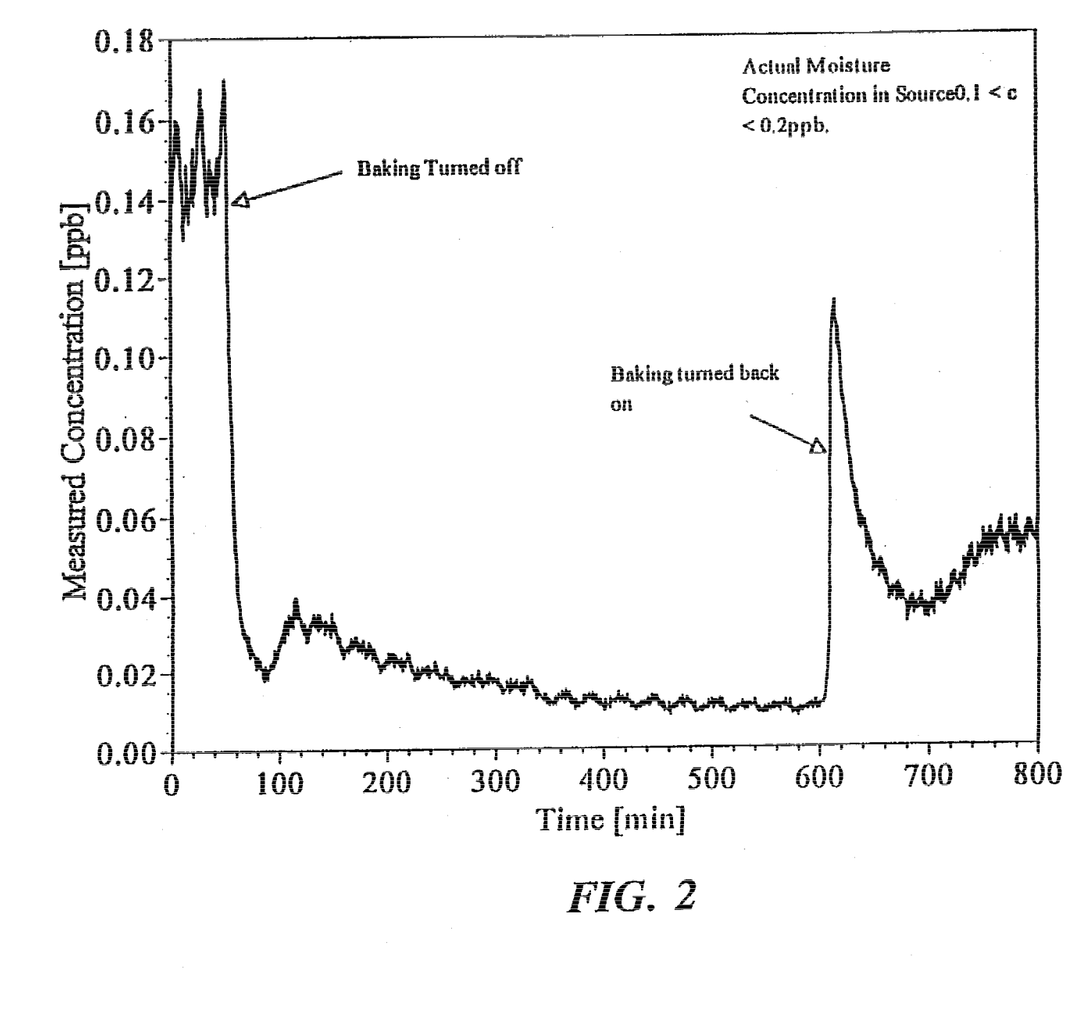
FIG. 2 is a graph of moisture concentration versus time for a sampling line, showing the effect of sampling line baking on measured moisture concentration.

FIG. 2 illustrates an example in which the sampling line baking is terminated after about 500 minutes, which prompts a substantial decrease in the measured moisture level. The actual source gas concentration is about 0.15 ppb. As can be seen from this figure, the measured level is well below the actual impurity value for an extended period of time.

Figure 3:
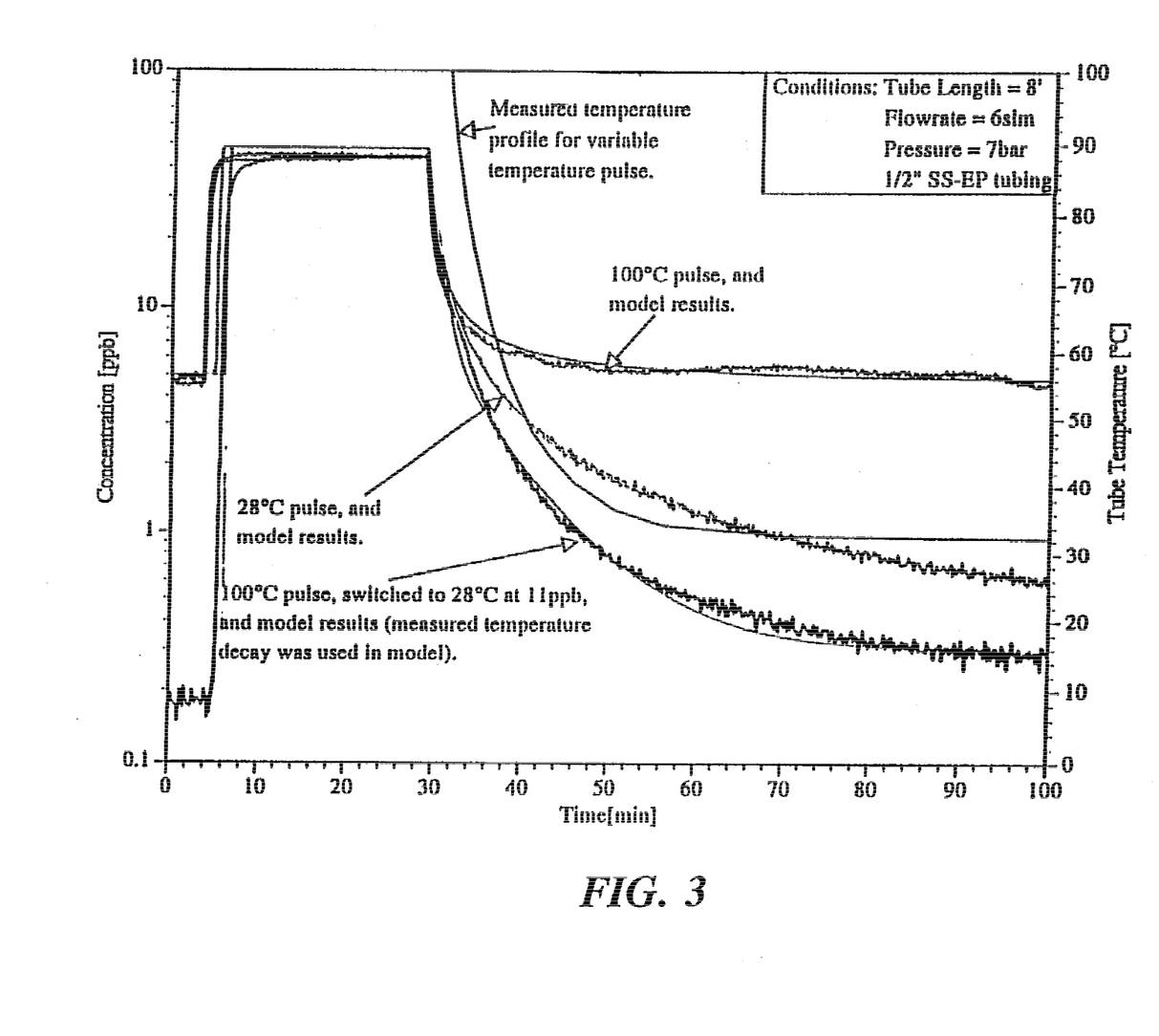
FIG. 3 is a graph of moisture concentration versus time for a sampling line, showing a comparison of model and experimental results for various sampling line baking strategies.

In FIG. 3, both experimental and simulation results are shown for three sampling line baking strategies. The three baking strategies include a continuous 28° C. pulse (no baking), a continuous 100° C. pulse and a variable 100° C./28° C. pulse. In the variable pulse baking strategy, the sampling line temperature was switched from 100° C. to 28° C. after a measured water vapor concentration of 11 ppb was attained. For the simulations, it was assumed that the temperature of the sampling line was uniform (although the temperature varied with time).

The water vapor concentration of the source gas entering the sampling line was 0.25 ppb. To obtain a proper comparison of the experimental and simulation data, the sampling line drydown was simulated as the response after contamination of the sampling line with 50 ppb water vapor, followed by purging with the 0.25 ppb source gas. It can be clearly seen that the variable pulse baking method achieved this level more rapidly than either the continuous 28° C. pulse (no baking case) or the continuous 100° C. pulse approaches.

Furthermore, as can be seen from FIG. 3, the simulation results track the actual results extremely closely. This indicates that the modeling approach can accurately predict the effects of a baking strategy on measured concentration in the sampling line.

The baking strategy should be designed to bring the measured impurity level to that of the gas entering the sampling line as quickly as possible without an artificially low level being measured. Such a baking strategy is called the "optimum baking strategy." The use of computer simulation to predict the moisture response is useful in determining the optimum baking strategy, thereby preventing the measurement of artificially low values.

The physical phenomena that is being taken advantage of in the invention is the variation of the impurity adsorption isotherm on the inner surface of the sampling line as a function of temperature. At temperatures greater than room temperature, the capacity of a metal surface to hold moisture (e.g., in units of number of molecules/$cm^2$) is reduced compared to the capacity at room temperature. As a result, when baking temperature is reduced, for example to room temperature, the effective adsorption isotherm at the lower temperature becomes effective. Because of the lower temperature adsorption isotherm, the metal surface acts as a moisture getterer. Consequently, the measured moisture level in the vapor phase becomes decreased compared to the measured level at the higher baking temperature.

According to the inventive method, after the sampling line baking is concluded, the impurity concentration profile of the line contains a first region in which the vapor phase impurity concentration is less than the vapor phase impurity concentration of the gas entering the sample line, and a second region in which the vapor phase impurity concentration is greater than the vapor phase impurity concentration of the gas entering the sampling line.

The effectiveness of the baking strategy can be understood by a comparison of concentration profiles in a sampling line at various times during drydown of the line. Estimated impurity concentration profiles can be determined from numerical simulation and require the knowledge of the adsorption isotherms for the impurity to be measured. Methods for measuring the adsorption isotherm as well as methods of simulating baking strategies to determine corresponding concentration profiles in gas lines are known, and are described and validated in the literature.

Figure 4:
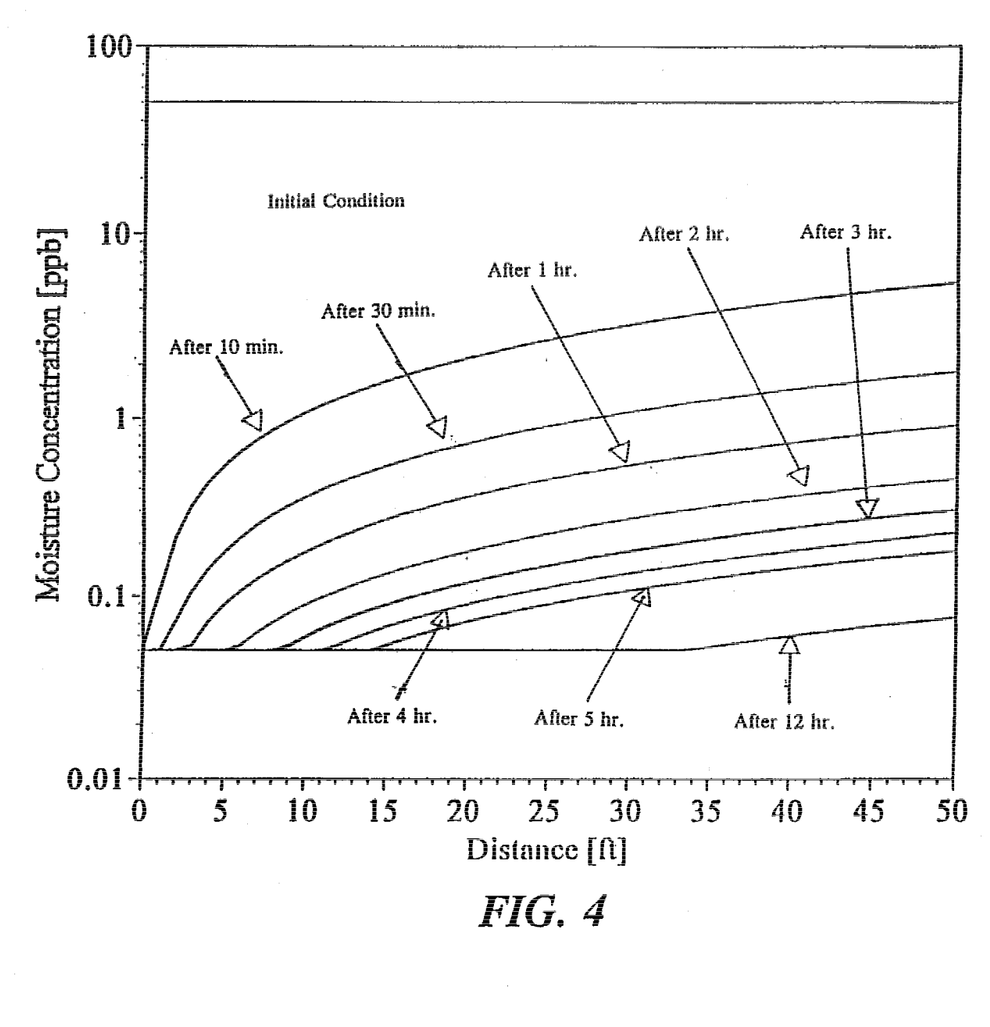
FIG. 4 is a graph of moisture concentration versus distance along the length of a sampling line with no sampling line baking.
Figure 5:
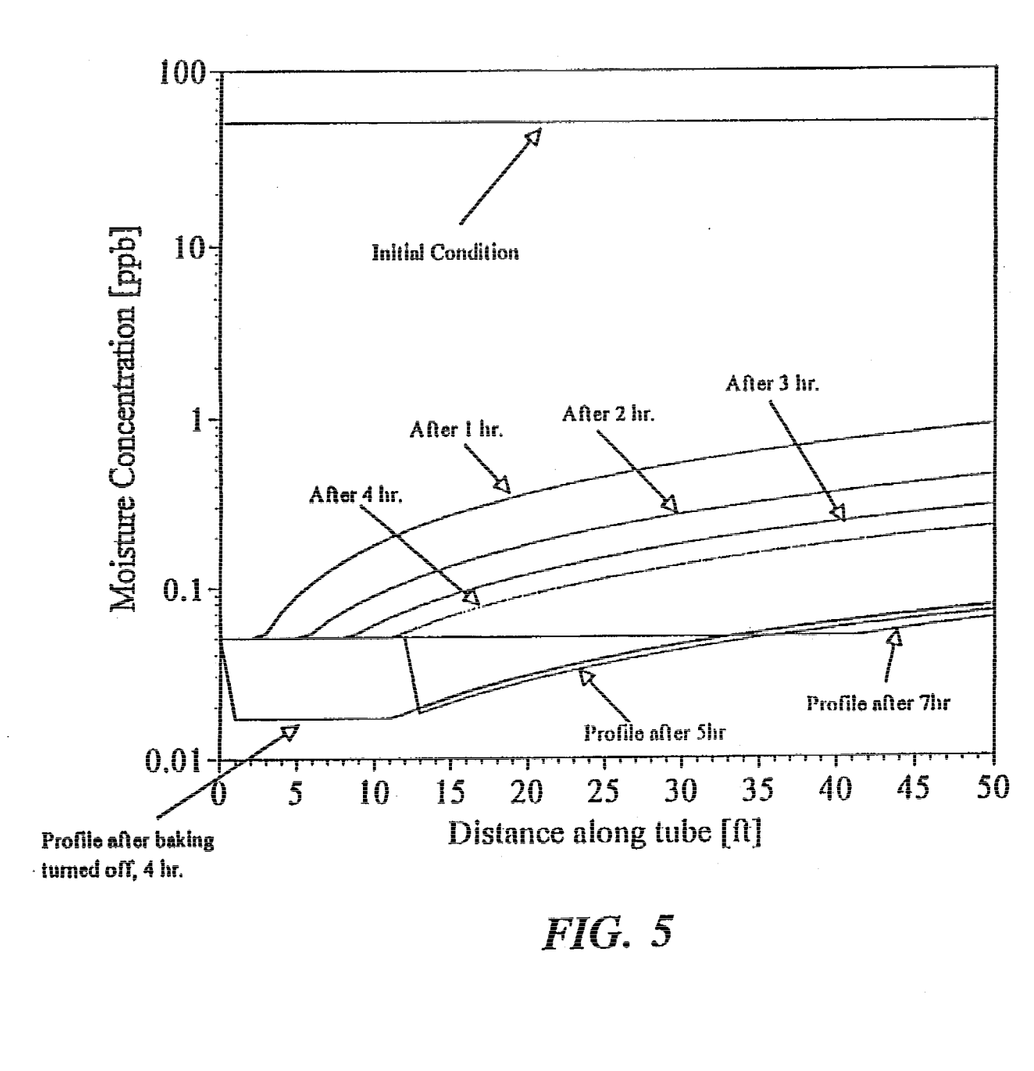
FIG. 5 is a graph of moisture concentration versus distance along the length of a sampling line for various sampling line baking strategies.
Figure 6:
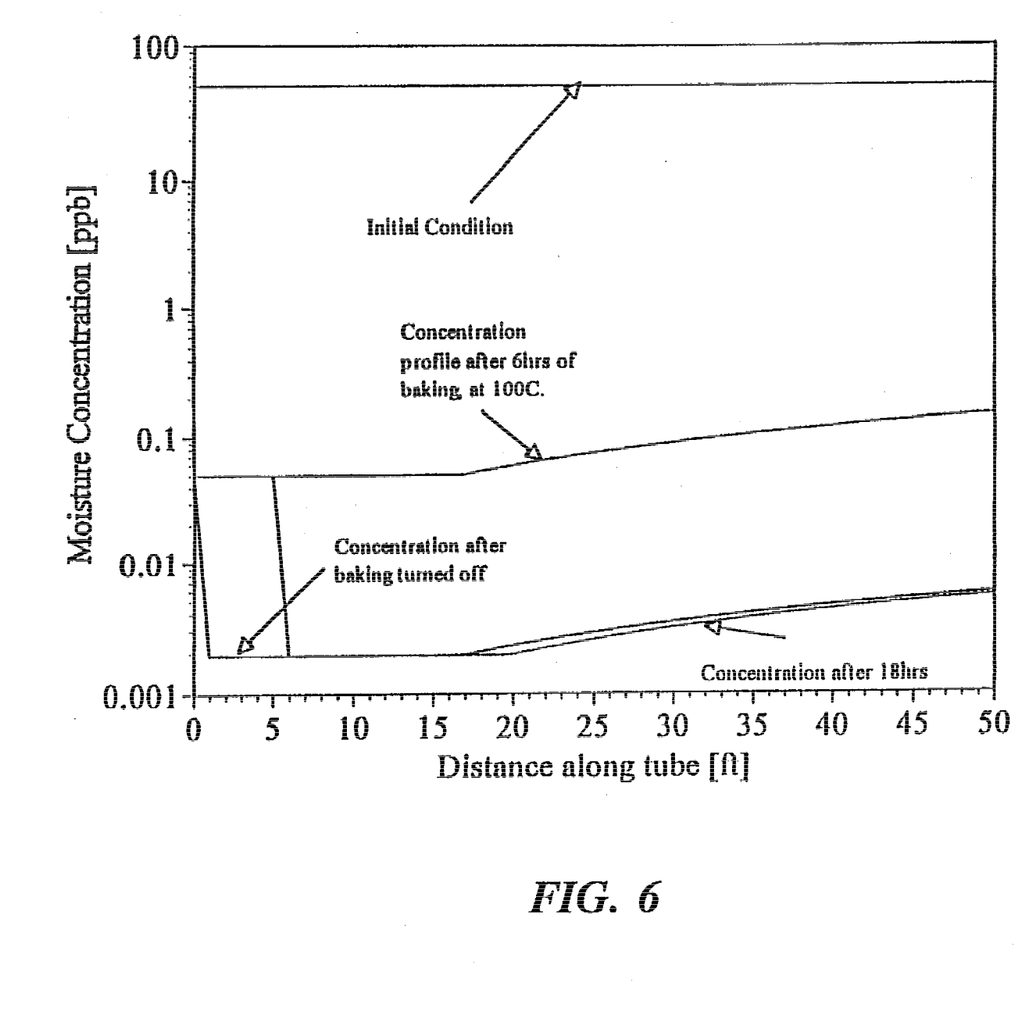
FIG. 6 is a graph of moisture concentration versus distance along the length of a sampling line for various sampling line baking strategies.

FIGS. 4–6 illustrate simulated concentration profiles along the length of a 50 foot sampling line for various baking strategies. The gas sample flow rate was assumed to be 10 slm at a pressure of 7 Bar. For the simulations, it was assumed that the sampling line was initially equilibrated at 50 ppb moisture, and that the purity of the gas entering the sampling line was 0.05 ppb.

FIG. 4 shows the evolution of moisture concentration profiles along the length of the sampling line over a period of 12 hours wherein the sampling line is purged with the gas and is not baked. The sampling line inlet is located at the origin of the x-axis, and the gas outlet is located at the 50 foot point on that axis. As the gas is purged through the sampling line, the vapor phase impurity concentration in the sampling line in the vicinity of the gas inlet first approaches the actual vapor phase concentration of the impurity in the gas being introduced into the sampling line. With an increase in purging time, that region of the sampling line at the same concentration as the gas entering the sample line (i.e., the purging wave) extends downstream from the gas inlet. After 12 hours of purging, the purging wave has not yet reached the gas outlet. That is, the concentration of water vapor at the sampling line outlet remains elevated relative to the concentration of the water vapor in the gas entering the sampling line.

FIG. 5 illustrates the effects of baking strategy on the evolution of water vapor concentration profiles in a sampling line. The sampling line is baked at 50° C. for 4 hours, and then the baking is terminated. The evolution of the sampling line concentration profiles is qualitatively similar to the profiles shown in FIG. 4 (purging without baking) for the first 4 hours. However, when the temperature of the line is decreased upon termination of sampling tube baking, the concentration profile changes. When the baking is terminated (see, profile after baking turned off, 4 hr), there is a first region extending from the gas inlet to a distance of about 34 feet along the sampling line in which the measured vapor phase concentration is below that of the source gas introduced into the sampling line (i.e., 0.05 ppb). This first region effectively acts as a moisture getterer. That is, there is a net adsorption of water vapor on the inner surface of the sampling line in the first region.

In a second region of the sampling line, located downstream from the first region and extending to the gas outlet, the water vapor concentration is elevated with respect to the concentration of the source gas being introduced into the sampling line. This second region is considered to be in a purging state as a result of its elevated concentration relative to the source gas concentration.

The first region of the line is effectively being "contaminated" with gas having the same purity as the gas source or gas distribution system, while the second region of the gas sampling line continues to be purged. Since the length of the second region immediately after termination of baking (i.e., 16 feet) is effectively shorter than the length of the entire sampling line (i.e., 50 feet), the dry down time is effectively decreased compared to the situation in which baking is not used.

At 7 hours into the baking strategy, the measured vapor phase impurity concentration at the gas outlet end of the sampling line approaches that of the gas being introduced into the sampling line. When compared with the concentration profiles illustrated in FIG. 4, it is clear that an improvement of about 5 hours is realized over the situation in which baking is not used.

FIG. 6 illustrates the effect of overbaking the sampling line. The baking strategy in this example includes baking the gas sampling line to 100° C. for a period of 6 hours, and then terminating the baking. Upon conclusion of baking, the concentration profile along the entire length of the sampling line decreases to less than the impurity concentration in the gas introduced into the sampling line. Because the capacity of the sampling line internal surfaces to adsorb water vapor (i.e., the gettering capacity) is very high along the entire length of the sampling line, the rate of propagation of the source gas concentration level (i.e., the contamination wave) through the sampling line is very slow. Consequently, the moisture concentration measured at the gas outlet of the sampling line is lower than the impurity concentration of the gas introduced into the sampling line for an extended period of time. If care is not taken, the gas source or gas distribution system can easily be certified at a lower than actual impurity level.

A comparison of the impurity concentration profiles shown in FIGS. 4–6 makes clear that in order to decrease measurement time for a gas source or a gas distribution system, a controlled sampling line baking strategy should be implemented. The baking strategy should be designed such that, subsequent to the termination of baking, there are two regions in the sampling line. In a first region, extending from the sampling tube gas inlet to a point downstream from the inlet, the impurity concentration is less than the impurity concentration of the gas introduced into the sampling line. In the second region, extending from a point downstream from the first region to the gas outlet of the sampling line, the impurity concentration is greater than the impurity concentration of the gas introduced into the sampling line.

Furthermore, the baking strategy should be designed such that the time required for the first region of the sampling line to be brought to the impurity level of the gas introduced into the sampling line is less than the purging time required to lower the impurity concentration in the second region to that impurity level. In other words, the baking strategy should be designed such that the rate of propagation of the source gas contamination wave is sufficiently fast that it reaches the purging wave before the purging wave exits the gas sampling line. In order to minimize the impurity measurement time, a baking strategy should be selected such that the point at which the contamination wave reaches the normal purging wave is located as closely as possible to the gas outlet of the sampling line.

The impurity measurement is performed until the impurity level becomes stabilized. That is, the true impurity level is reached when there is no further decrease in the measured level. To ensure that the impurity level is stabilized, the flowrate through the sampling line can be measured at a plurality of gas flow rates. For example, measurements can be made at the sampling flowrate, one half the sampling flowrate, and double the sampling flowrate. If the measured level is the same for the three measurements, the impurity level can be assumed to be stabilized.

The use of a simulation program is very effective in determining the optimum baking strategy. A precise knowledge of the impurity concentration in the gas entering the sampling tube is not required. However, a liberal estimate should be used to determine the baking strategy. This estimate can be based on, for example, past experience or the impurity level for which the plant and/or distribution system is designed for. Alternatively, information from other measurements taken in the distribution system can be used. The specific conditions governing the sampling (e.g., flowrate, pressure, length of gas sampling tube, gas sampling line surface properties, gas sampling line diameter, baking capabilities and ambient temperature) can be used in the simulation program to devise an effective or optimum baking strategy. As demonstrated by the above examples, a time savings of greater than 50% compared to prior methods can be achieved by means of the inventive method.

While the invention has been described in detail with reference to specific embodiments thereof, it will be apparent to one skilled in the art that various changes and modifications can be made, and equivalents employed, without departing from the scope of the appended claims.

What is claimed is:

1. A method for rapidly determining an impurity level in a gas source, comprising:

(a) providing a gas source;

(b) providing a measurement tool for measuring an impurity level in a gas flowing from the gas source, wherein the measurement tool is in communication with the gas source through a sampling line, the sampling line having a gas inlet disposed upstream from a gas outlet; and (c) baking the sampling line according to a baking strategy, such that when the baking is terminated, a concentration profile of the impurity in the sampling line contains a first region extending from the gas inlet to a point downstream from the inlet, in which the vapor phase concentration of the impurity is less than the vapor phase concentration of the impurity in the gas entering the sampling line, and a second region downstream from the first region extending to the gas outlet in which the vapor phase concentration of the impurity is greater than the vapor phase concentration of the impurity in the gas entering the sampling line.

2. The method for rapidly determining an impurity level according to claim 1, wherein a simulation program is employed to determine the baking strategy.

3. The method for rapidly determining an impurity level according to claim 1, wherein the measurement tool is an atmospheric pressure ionization mass spectrometer.

4. The method for rapidly determining an impurity level according to claim 1, wherein the impurity is water vapor.

5. The method for rapidly determining an impurity level according to claim 1, wherein the gas is nitrogen, helium, argon, or oxygen.

6. The method for rapidly determining an impurity level according to claim 1, wherein the impurity level is measured until the measured impurity level becomes stabilized.

7. A method for rapidly determining an impurity level in a gas distribution system, comprising:

(a) providing a gas distribution system for delivering a gas to a point of use, the gas distribution system being connected to a gas source;

(b) providing a measurement tool for measuring an impurity level in a gas flowing through the gas distribution system, wherein the measurement tool is in communication with the gas distribution system through a sampling line, the sampling line having a gas inlet disposed upstream from a gas outlet; and (c) baking the sampling line according to a baking strategy, such that when the baking is terminated, a concentration profile of the impurity in the sampling line contains a first region extending from the gas inlet to a point downstream from the inlet, in which the vapor phase concentration of the impurity is less than the vapor phase concentration of the impurity in the gas entering the sampling line, and a second region downstream from the first region extending to the gas outlet in which the vapor phase concentration of the impurity is greater than the vapor phase concentration of the impurity in the gas entering the sampling line.

8. The method for rapidly determining an impurity level according to claim 7, wherein a simulation program is employed to determine the baking temperature.

9. The method for rapidly determining an impurity level according to claim 7, wherein the measurement tool is an atmospheric pressure ionization mass spectrometer.

10. The method for rapidly determining an impurity level according to claim 7, wherein the impurity is water vapor.

11. The method for rapidly determining an impurity level according to claim 7, wherein the point of use of the gas is a semiconductor processing tool.

12. The method for rapidly determining an impurity level according to claim 7, wherein the impurity level measurement is performed at a plurality of points along the gas distribution system.

13. The method for rapidly determining an impurity level according to claim 7, wherein the gas is nitrogen, helium, argon, or oxygen.

14. The method for rapidly determining an impurity level according to claim 7, wherein the impurity level is measured until the measured impurity level becomes stabilized.

* * * * *